US012582814B2

(12) United States Patent
Xie et al.

(10) Patent No.: US 12,582,814 B2
(45) Date of Patent: *Mar. 24, 2026

(54) BLOOD PUMP AND DRIVING DEVICE THEREOF

(71) Applicant: Shenzhen Core Medical Technology Co., Ltd., Shenzhen (CN)

(72) Inventors: Duanqing Xie, Shenzhen (CN); Shunzhou Yu, Shenzhen (CN)

(73) Assignee: Shenzhen Core Medical Technology Co., Ltd. (CN)

( * ) Notice: Subject to any disclaimer, the term of this patent is extended or adjusted under 35 U.S.C. 154(b) by 279 days.

This patent is subject to a terminal disclaimer.

(21) Appl. No.: 18/280,394

(22) PCT Filed: Nov. 15, 2022

(86) PCT No.: PCT/CN2022/132045
§ 371 (c)(1),
(2) Date: Sep. 5, 2023

(87) PCT Pub. No.: WO2023/098470
PCT Pub. Date: Jun. 8, 2023

(65) Prior Publication Data
US 2024/0149049 A1     May 9, 2024

(30) Foreign Application Priority Data

Dec. 3, 2021    (CN) .......................... 202111474226.1

(51) Int. Cl.
*A61M 60/419*        (2021.01)
*A61M 60/122*        (2021.01)
(Continued)

(52) U.S. Cl.
CPC ..... *A61M 60/419* (2021.01); *A61M 2205/103* (2013.01); *A61M 2205/8262* (2013.01)

(58) Field of Classification Search
CPC .. A61M 60/422; A61M 60/216; A61M 60/13; A61M 60/416; A61M 60/825;
(Continued)

(56) References Cited

U.S. PATENT DOCUMENTS 5,851,174  A * 12/1998  Jarvik ................. A61M 60/812
600/16
6,234,772  B1     5/2001  Wampler et al.
(Continued)

FOREIGN PATENT DOCUMENTS

CN          101034838 A        9/2007
CN          202889089 U        4/2013
(Continued)

OTHER PUBLICATIONS

Extended European Search Report including Written Opinion for Application No. 22900275.3 dated Mar. 6, 2025, pp. 1-15.
(Continued)

*Primary Examiner* — Jon Eric C Morales
(74) *Attorney, Agent, or Firm* — Lerner David LLP

(57)             ABSTRACT
A blood pump (100) and a driving device thereof. The driving device (10) comprising a driving shell (11), a rotor (12) and a stator mechanism (13); the rotor (12) comprises a rotating shaft (121) and a first magnet (122), one end of the rotating shaft (121) is accommodated in the driving shell (11), and the first magnet (122) is fixedly connected with the rotating shaft (121); the stator mechanism is accommodated in the driving shell (11), the stator mechanism (13) comprises a driving stator (131), the driving stator (131) and the rotating shaft (121) are provided at intervals along the axis of the rotating shaft (121), and the driving stator (131) can generate a rotating magnetic field interacting with the first magnet (122), so that the first magnet (122) can drive the rotating shaft (121) to rotate.

18 Claims, 15 Drawing Sheets

(51) Int. Cl.
*A61M 60/216* (2021.01)
*A61M 60/416* (2021.01)

(58) Field of Classification Search
CPC .............. A61M 60/818; A61M 60/804; A61M
60/135; A61M 60/857; A61M 60/81;
A61M 60/829; A61M 60/237; A61M
60/205; A61M 60/221; A61M 2205/103;
A61M 60/419; A61M 2205/0211; A61M
60/148; A61M 60/174; A61M 60/139;
A61M 2205/0222; A61M 2205/0233;
A61M 2205/3606; A61M 60/242; A61M
60/414; A61M 60/802; A61M 60/403;
A61M 2205/04; A61M 60/824; A61M
60/126; A61M 60/82; A61M 2205/02;
A61M 60/232; A61M 60/411; A61M
60/806; A61M 2207/00; A61M 60/122;
A61M 60/855; A61M 2205/0283; A61M
60/538; A61M 2205/8262; A61M 60/50;
A61M 2205/025; A61M 60/508; A61M
60/859; A61M 60/178; A61M 60/871;
A61M 60/88; A61M 60/117; A61M
60/40; F04D 29/048; F04D 25/0606
See application file for complete search history.

(56) References Cited

U.S. PATENT DOCUMENTS

| | | |
|---|---|---|
| 2004/0141286 A1 | 7/2004 | Willmer et al. |
| 2019/0298902 A1 | 10/2019 | Siess et al. |
| 2020/0306434 A1 | 10/2020 | VanCamp et al. |
| 2021/0085954 A1 | 3/2021 | Smith |
| 2022/0068559 A1 | 3/2022 | Zhou et al. |
| 2023/0144798 A1 | 5/2023 | Yu |
| 2023/0310834 A1 | 10/2023 | Yu |
| 2024/0149045 A1* | 5/2024 | Xie ...................... A61M 60/81 |

FOREIGN PATENT DOCUMENTS

| | | | |
|---|---|---|---|
| CN | 105641763 A | 6/2016 |
| CN | 108175884 A | 6/2018 |
| CN | 110195755 A | 9/2019 |
| CN | 110393846 A | 11/2019 |
| CN | 111840683 A | 10/2020 |
| CN | 112002545 A | 11/2020 |
| CN | 112107749 A | 12/2020 |
| CN | 112472999 A | 3/2021 |
| CN | 112587792 A | 4/2021 |
| CN | 112791305 A | 5/2021 |
| CN | 214260372 U | 9/2021 |
| CN | 113559408 A | 10/2021 |
| CN | 114796845 A | 7/2022 |
| CN | 114796846 A | 7/2022 |
| EP | 3539584 A1 | 9/2019 |
| JP | H07336967 A | 12/1995 |
| JP | H08322194 A | 12/1996 |
| JP | 2002541985 A | 12/2002 |
| JP | 2004173489 A | 6/2004 |
| JP | 2012205349 A | 10/2012 |
| JP | 2019512336 A | 5/2019 |
| JP | 2022514881 A | 2/2022 |
| JP | 2023511326 A | 3/2023 |
| WO | 2020198035 A1 | 10/2020 |
| WO | 2023160422 A1 | 8/2023 |
| WO | 2023236717 A1 | 12/2023 |
| WO | 2023236759 A1 | 12/2023 |

OTHER PUBLICATIONS

International Search Report for PCT/CN2022/132045 mailed Feb. 14, 2023. 4 pgs.
Search Report dated Apr. 3, 2023 from Office Action for Chinese Application No. 202111474226 issued Apr. 6, 23. 3 pgs.(see p. 1-2, categorizing the cited references).

* cited by examiner

11

BLOOD PUMP AND DRIVING DEVICE THEREOF

CROSS-REFERENCE TO RELATED APPLICATIONS

This application is an U.S. national phase application under 35 U.S.C. § 371 based upon international patent application No. PCT/CN2022/132045 filed on Nov. 15, 2022, which itself claims priority to Chinese Patent Application No. 202111474226.1, filed on Dec. 3, 2021, the entire content of which is incorporated herein by reference.

TECHNICAL FIELD

The present disclosure relates to the field of medical devices, and in particular, to a blood pump and a driving device.

BACKGROUND

Intravascular blood pump is a device designed to be inserted percutaneously into a patient's blood vessel and probed into the patient's heart as a left ventricular assist device or right ventricular assist device, and the intravascular blood pump may also be referred to as an intracardiac blood pump.

The conventional blood pump mainly includes an impeller and a driving device that drives the impeller to rotate. Driven by the driving device, the impeller transfers blood from a blood inflow port of the blood pump to a blood outflow port. However, in this process, the power consumption of the driving device is higher, which results in a greater energy consumption of the blood pump.

SUMMARY

Accordingly, the present disclosure provides a blood pump with low power consumption and a driving device thereof, which can reduce the power consumption of the blood pump.

The driving device includes:

a driving housing;

a rotor including a rotating shaft and a first magnet, one end of the rotating shaft being accommodated in the driving housing, the first magnet being fixedly connected to the rotating shaft; and a stator mechanism accommodated in the driving housing, the stator mechanism including a driving stator, the driving stator and the rotating shaft being spaced along an axis of the rotating shaft, the driving stator being capable of generating a rotating magnetic field interacting with the first magnet, such that the first magnet is capable of driving the rotating shaft to rotate about the axis of the rotating shaft.

The driving device includes:

a driving housing;

a rotor including a rotating shaft, a first magnet, and a second magnet, the rotating shaft being capable of being rotatably mounted on the driving housing, both of the first magnet and the second magnet being fixedly connected to the rotating shaft; and a stator mechanism including a driving stator and a power stator, wherein the driving stator and the power stator are arranged along an axis of the rotating shaft, the driving stator and the rotating shaft are spaced along the axis of the rotating shaft, the driving stator is capable of generating a rotating magnetic field that drives the first magnet to rotate, the power stator is capable of generating a rotating magnetic field that drives the second magnet to rotate, wherein the driving stator comprises a first magnetic core and a first coil, the power stator comprises a second magnetic core and a second coil, each of the first magnetic core and the second magnetic core comprises a magnetic column, the first coil is wound on the magnetic column of the first magnetic core, the second coil is wound on the magnetic column of the second magnetic core, a cross-sectional area of the magnetic column of the first magnetic core is greater than a cross-sectional area of the magnetic column of the second magnetic core.

The blood pump includes:

a driving device as described above;

an impeller fixedly connected to the rotating shaft and capable of rotating with the rotating shaft.

The details of one or more embodiments of the present invention are set forth in the accompanying drawings and the description below. Other features, objects and advantages of the present invention will become apparent from the description, the accompanying drawings, and the claims.

BRIEF DESCRIPTION OF THE DRAWINGS

To illustrate the technical solutions according to the embodiments of the present invention or in the prior art more clearly, the accompanying drawings for describing the embodiments or the prior art are introduced briefly in the following. Apparently, the accompanying drawings in the following description are only some embodiments of the present invention, and persons of ordinary skill in the art can derive other drawings from the accompanying drawings without creative efforts.

DETAILED DESCRIPTION OF THE EMBODIMENTS

The above objects, features and advantages of the present invention will become more apparent by describing in detail embodiments thereof with reference to the accompanying drawings. It should be understood that the specific embodiments described herein are merely illustrative of this application and are not intended to limit this application.

It should be noted that, when one element is referred to as "being fixed to" or "being disposed on" another element, the element may be directly on another element or there may be indirectly to that other element. When an element is referred to as "connected to" another element, it may be connected directly to another element or indirectly to that other element.

In addition, the terms "first" and "second" are used for descriptive purposes only, which cannot be construed as indicating or implying a relative importance, or implicitly specifying the number of the indicated technical features. Therefore, the defined "first" and "second" features may explicitly or implicitly include one or more of the features. In the description of the present disclosure, "plurality" means two, or at least two, unless otherwise specifically defined.

In order to describe the technical solution of the present application, the following describes with reference to specific drawings and embodiments.

Figure 1:
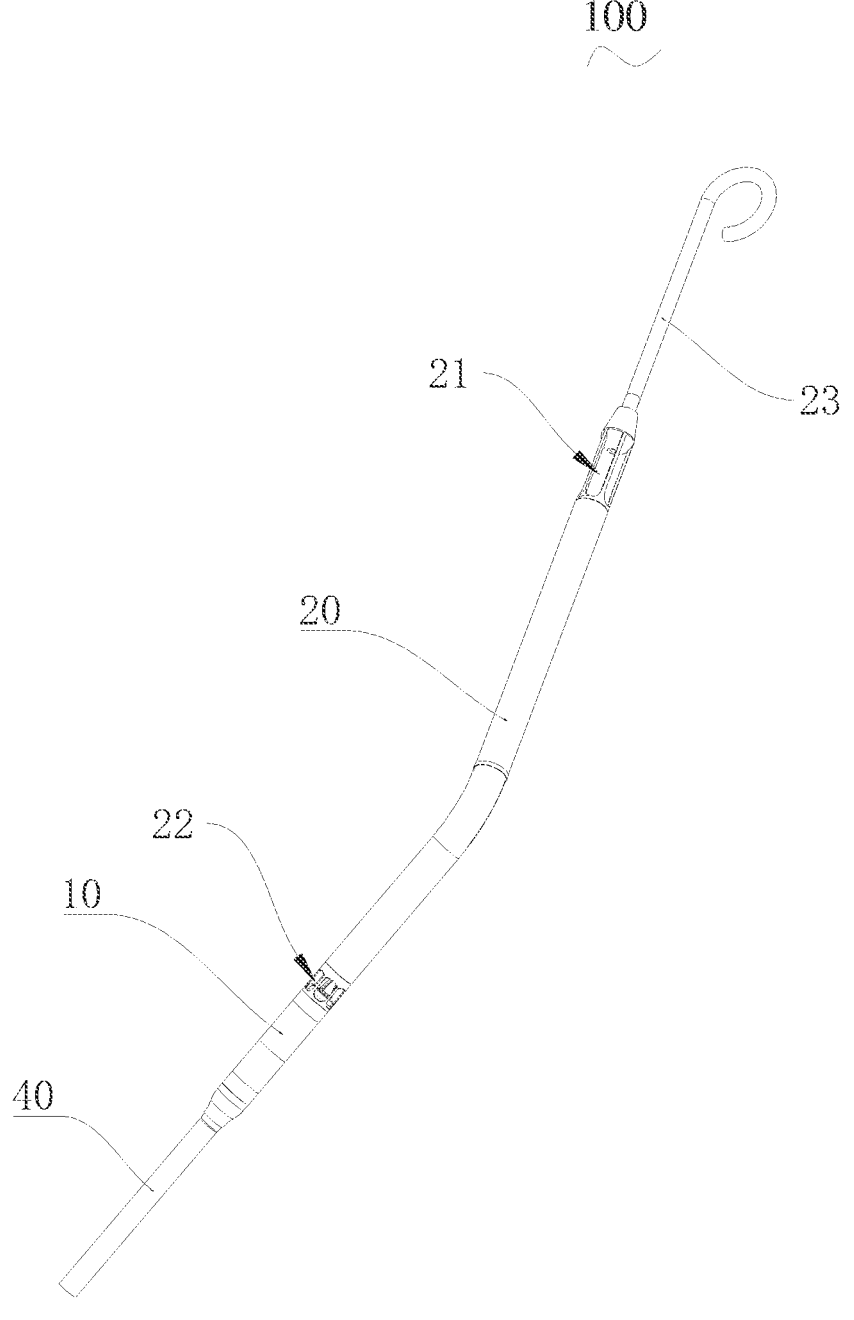
FIG. 1 is a structure schematic view of a blood pump according to an embodiment of the present disclosure.
Figure 2:
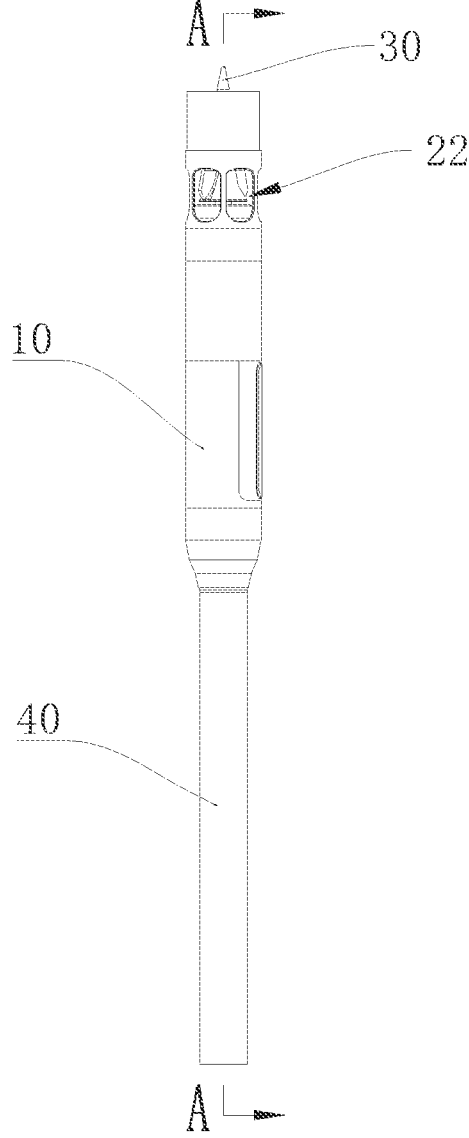
FIG. 2 is a partial schematic structural view of the blood pump shown in FIG. 1.
Figure 3:
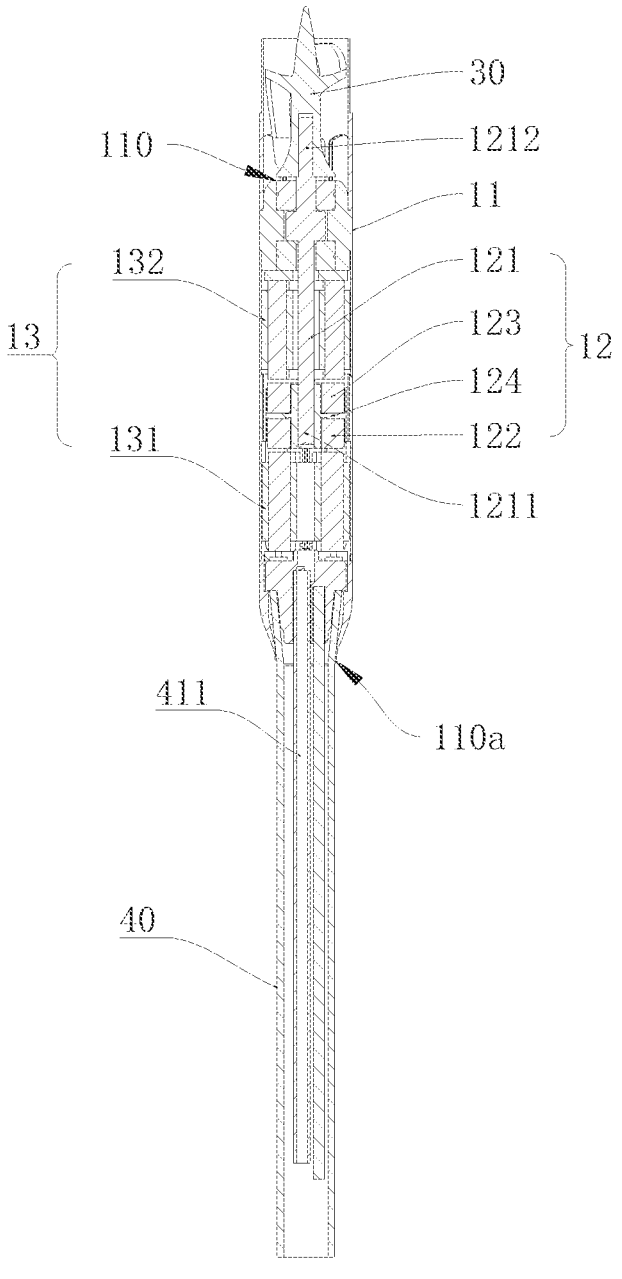
FIG. 3 is a cross-sectional view of the blood pump shown in FIG. 2 taken along the line A-A.

Referring to FIG. 1 to FIG. 3, an embodiment of the present application provides a blood pump 100, which includes a driving device 10, a sleeve assembly 20, and an impeller 30. The sleeve assembly 20 is connected to the driving device 10, the impeller 30 is rotatably received in the sleeve assembly 20, the impeller 30 is connected to the driving device 10, and the driving device 10 can drive the impeller 30 to rotate, so as to achieve the blood pumping function of the blood pump 100.

Specifically, the sleeve assembly 20 has an inflow port 21 and an outflow port 22. In one embodiment, the sleeve assembly 20 extends through a heart valve, such as an aortic valve. The inflow port 21 is located within the heart, and the outflow port 22 and the driving device 10 are located in a blood vessel, such as the aorta outside the heart. As the impeller 30 rotates, blood flows from the inflow port 21 into the sleeve assembly 20, and flows out of the sleeve assembly 20 from the outflow port 22.

More specifically, one end of the sleeve assembly 20 is connected to the driving device 10, and the other end may be provided with a pigtail catheter 23, which is configured to stabilize the position of the blood pump 100 in the heart, so as to provide a non-invasive support for the heart tissue.

Specifically, the pigtail catheter 23 is of a hollow structure. The material of the pigtail catheter 23 is selected from at least one of polyurethane, nylon, polyethylene, polyether block polyamide PEBAX and latex material.

Further, the blood pump 100 further includes a catheter assembly 40, and the catheter assembly 40 is connected to the driving device 10. Supply lines are provided in the catheter assembly 40, and the supply lines include a perfusion pipeline 411 configured to supply the driving device 10 with perfusion liquid, and an electrical connection line configured to supply power to the driving device 10 and/or to be electrically connected to an external electric appliance (such as an external controller, etc.). Specifically, the perfusion solution may be, for example, normal saline, normal saline containing heparin, or glucose, etc.

The driving device 10 is in transmission connection with the impeller 30, and the driving device 10 can drive the impeller 30 to rotate. The driving device 10 includes the driving housing 11, a rotor 12, and a stator mechanism 13.

The driving housing 11 is substantially cylindrical. The impeller 30 is disposed outside driving housing 11. The driving housing 11 has a communication port 110, and the communication port 110 is located on a side of the driving housing 11 adjacent to the impeller 30. Specifically, the sleeve assembly 20 and the catheter assembly 40 are fixedly connected to both ends of the driving housing 11, respectively, and the communication port 110 communicates the driving housing 11 with the sleeve assembly 20. The perfusion pipeline 411 in the catheter assembly 40 is in communication with the driving housing 11. The perfusion liquid supplied in the perfusion pipeline 411 can flow through the interior of the driving housing 11, and flow into the sleeve assembly 20 from the communication port 110, so as to prevent the blood from permeating into the driving housing 11 from the communication port 110 of the driving housing 11.

Specifically, the driving housing 11 also has a docking port 110a, which can be in communication with the perfusion pipeline 411 of the blood pump 100, such that the perfusion liquid can flow through the driving housing 11 through the perfusion pipeline 411, and flow into the sleeve assembly 20 from the communication port 110. In the illustrated embodiment, the catheter assembly 40 is docked with the docking port 110a of the driving housing 11, and the perfusion pipeline 411 of the catheter assembly 40 extends through the docking port 110a with the catheter assembly 40, and is partially accommodated in the driving housing 11.

The rotor 12 is rotatably mounted in the driving housing 11. The rotor 12 is fixedly connected to the impeller 30, and the rotor 12 can drive the impeller 30 to rotate. The rotor 12 includes a rotating shaft 121 and a first magnet 122. One end of the rotating shaft 121 is accommodated in the driving housing 11, the other end is located outside the driving housing 11 and is fixedly connected to the impeller 30. The rotating shaft 121 is rotatable relative to the driving housing 11. The first magnet 122 is fixedly connected to the rotating shaft 121. Specifically, the rotating shaft 121 can rotatably extend through the communication port 110.

Specifically, the rotating shaft 121 is made of a material such as ceramic or stainless steel, for example, Zirconia Toughened Aluminum (ATZ) or SUS316L, so as to avoid fracture of the rotating shaft 121.

The stator mechanism 13 is accommodated in the driving housing 11, and the stator mechanism 13 can drive the rotor 12 to rotate. The stator mechanism 13 includes a driving stator 131, and the driving stator 131 and the rotating shaft 121 are spaced along the axis of the rotating shaft 121, that is, the rotating shaft 121 does not extend through the driving stator 131. The driving stator 131 is capable of generating a rotating magnetic field interacting with the first magnet 122, such that the first magnet 122 can drive the rotating shaft 121 to rotate about the axis of the rotation shaft 121, thereby driving the impeller 30 to rotate. Specifically, the axis of the rotating shaft 121 is a rotation axis of the rotating shaft 121.

Figure 4:
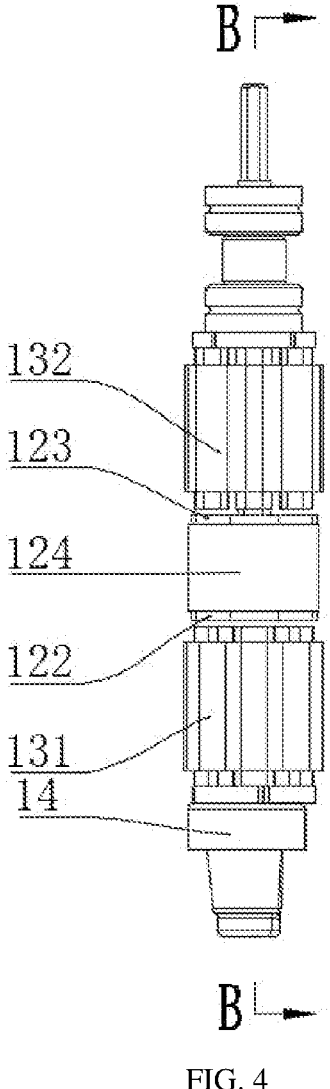
FIG. 4 is a schematic structural view of the driving device of the blood pump shown in FIG. 2 after omitting the driving housing.
Figure 5:
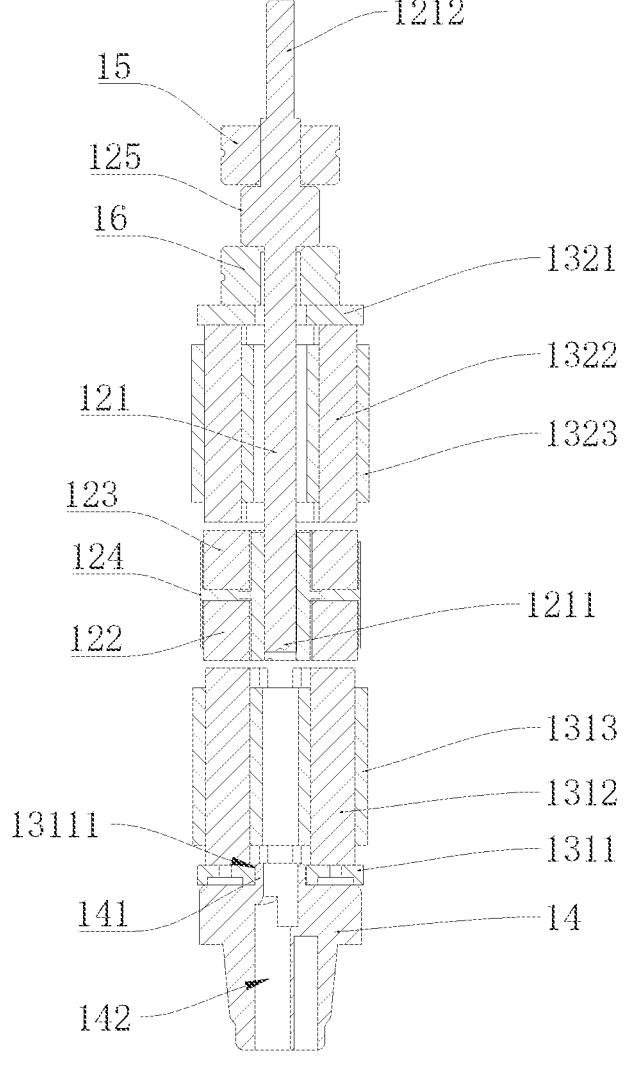
FIG. 5 is a cross-sectional view of the driving device shown in FIG. 4 taken along the line B-B.

Referring to FIG. 4 and FIG. 5, specifically, the driving stator 131 includes a first back plate 1311, a plurality of first magnetic cores 1312, and a plurality of first coils 1313 respectively wound around the first magnetic cores 1312. The first back plate 1311 is fixed in the driving housing 11. The plurality of the first magnetic cores 1312 are spaced one cycle around the axis of the rotating shaft 121. Specifically, an extending direction of each of the first magnetic cores 1312 is parallel to the axis of the rotating shaft 121. One end of each of the first magnetic cores 1312 is fixedly connected to the first back plate 1311, and the other end extends in a direction adjacent to the first magnet 122. The first coils 1313 are capable of generating a rotating magnetic field interacting with the first magnet 122, thereby causing the first magnet 122 to rotate to drive the impeller 30 to rotate.

It should be noted that, in some embodiments, the driving stator 131 may not have the first back plate 1311. The first back plate 1311 functions to close the magnetic circuit to promote and increase the generation of the magnetic flux of the driving stator 131 and improve the coupling capacity. Since the first back plate 1311 can increase the magnetic flux, the first back plate 1311 is provided to reduce the overall diameter of the blood pump 100. The material of the first back plate 1311 is the same as that of the first magnetic cores 1312. In some embodiments, both of the first back plate 1311 and the first magnetic cores 1312 are made of soft magnetic materials such as cobalt steel, etc.

In one embodiment, the driving device 10 further includes a fixing member 14 fixed in the driving housing 11. The fixing member 14 is provided with a positioning column 141, the first back plate 1311 is provided with a positioning hole 13111, and the positioning column 141 extends through the positioning hole 13111, so as to facilitate positioning and mounting of the driving stator 131. The axis of the positioning column 141 coincides with the axis of the rotating shaft 121.

Specifically, the fixing member 14 is provided with a through hole 142 that is in communication with an inner cavity of the driving housing 11, and the through hole 142 is configured to accommodate one end of the perfusion pipeline 411 adjacent to the impeller 30.

According to the driving device provided by the embodiment of the present disclosure, by arranging the driving stator 131 to be spaced apart from the rotating shaft 121 in the axial direction, the cross-section area of the magnetic core for the driving stator 131 is set to be large. The larger the cross-section area of the magnetic core is, the greater the magnetic flux generated by the driving stator 131 is, the greater torque for the first magnet 122 is. The current required when the driving stator 131 drives the rotating shaft 121 to rotate is also correspondingly reduced, which is beneficial to reduce the power consumption of the entire blood pump 100 and reduce the generated heat. Therefore, the blood pump 100 utilizing the above-described driving device 10 can have lower power consumption and less heat generation.

Further, the rotor 12 further includes a second magnet 123, and the second magnet 123 is fixedly connected to the rotating shaft 121. The stator mechanism 13 further includes a power stator 132. The power stator 132 and the driving stator 131 are disposed along the axis of the rotating shaft 121, and the power stator 132 is located more adjacent to the impeller 30 than the driving stator 131. In other words, in the extending direction of the rotating shaft 121, the power stator 132 is disposed between the impeller 30 and the driving stator 131. The rotating shaft 121 can rotatably extend through the power stator 132, and the power stator 132 can generate a rotating magnetic field interacting with the second magnet 123. The driving stator 131 and the power stator 132 can drive the first magnet 122 and the second magnet 123 to rotate, respectively, and the driving stator 131 and the power stator 132 can cooperatively drive the rotating shaft 121 to rotate about the axis of the rotating shaft 121, so as to drive the impeller 30 to rotate, thereby providing a larger driving force for the rotation of the impeller 30.

In the illustrated embodiment, the first magnet 122 and the second magnet 123 are disposed between the driving stator 131 and the power stator 132. Specifically, the rotor 12 further includes a flywheel 124 fixed to the rotating shaft 121, the flywheel 124 is located between the power stator 132 and the driving stator 131, and both of the first magnet 122 and the second magnet 123 are disposed on the flywheel 124.

Specifically, an end of the rotating shaft 121 away from the impeller 30 is a first end 1211, and an end of the rotating shaft 121 adjacent to the impeller 30 is a second end 1212. The flywheel 124 is fixedly sleeved on the first end 1211 of the rotating shaft 121. The flywheel 124 and the rotating shaft 121 may be integrally formed, or may be fixed to the rotating shaft 121 by bonding, welding, or the like.

By providing the flywheel 124, the connection strength between the magnet and the rotating shaft 121 can be increased, and the rotation stability of the rotating shaft 121 can be improved. In addition, by arranging both of the first magnet 122 and the second magnet 123 on the flywheel 124, the vibration of the rotating shaft 121 during rotation can be reduced, and the rotating shaft 121 can be more stable during rotation.

Figure 6:
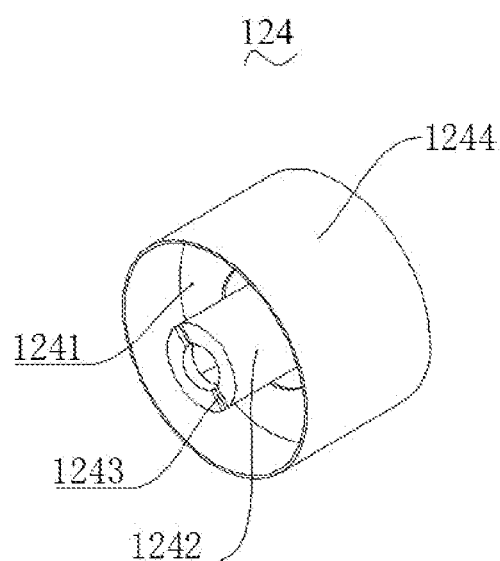
FIG. 6 is a perspective view of the flywheel of the driving device shown in FIG. 4.
Figure 7:
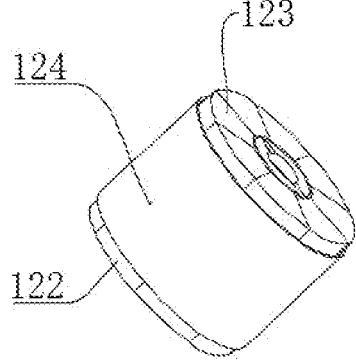
FIG. 7 is a perspective assembly view of the flywheel, the first magnet, and the second magnet of the driving device shown in FIG. 4.
Figure 8:
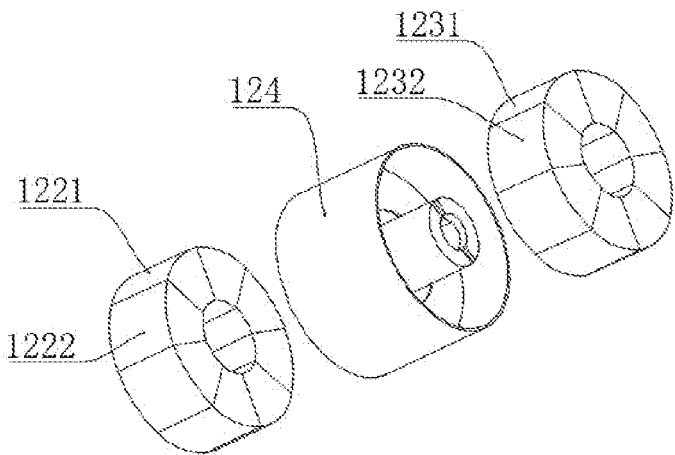
FIG. 8 is an exploded perspective view of the flywheel, the first magnet, and the second magnet shown in FIG. 7.
Figure 9:
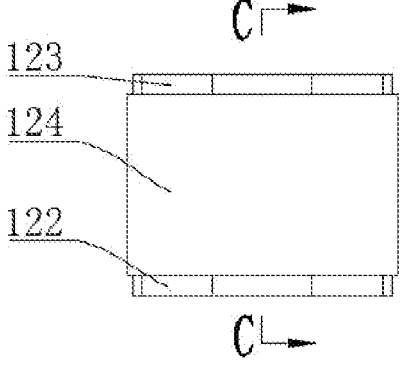
FIG. 9 is a front view of the flywheel, the first magnet, and the second magnet shown in FIG. 7.

More specifically, referring to FIG. 6, the flywheel 124 includes a disc-shaped portion 1241 and a tubular portion 1242. The tubular portion 1242 fixedly extends through a middle portion of the disc-shaped portion 1241, and is coaxial with the disc-shaped portion 1241. One end (that is, the first end 1211) of the rotating shaft 121 away from the impeller 30 is fixedly received in the tubular portion 1242. The first magnet 122 and the second magnet 123 are provided on opposite sides of the disc-shaped portion 1241, respectively, so as to facilitate assembly of the first magnet 122 and the second magnet 123, such that the first magnet 122 and the second magnet 123 can be better fixed to the rotating shaft 121.

Referring to FIG. 7 to FIG. 10, specifically, both the first magnet 122 and the second magnet 123 are ring-shaped Halbach array magnets. The first magnet 122 includes a plurality of first magnetic blocks 1221 whose magnetization directions are parallel to the axis of the first magnet 122, the second magnet 123 includes a plurality of second magnetic blocks 1231 whose magnetization directions are parallel to the axis of the second magnet 123. The plurality of second magnetic blocks 1231 and the plurality of first magnetic blocks 1221 are arranged on opposite sides of the disc-shaped portion 1241 surrounding the rotating shaft 121, respectively. In the extending direction of the rotating shaft 121, each of the second magnetic blocks 1231 is arranged opposite to one of the first magnetic blocks 1221, and sides of the oppositely arranged first magnetic blocks 1221 and second magnetic blocks 1231 facing the disc-shaped portion 1241 have opposite polarities. This arrangement can facilitate the mounting of the first magnet 122 and the second magnet 123, and avoid the problem of difficult assembly caused by the magnetic blocks of the first magnet 122 and the magnetic blocks of the second magnet 123 are mutually repulsive.

In some embodiments, the first magnet 122 further includes a plurality of third magnetic blocks 1222 magnetized in the circumferential direction of the first magnet 122. The plurality of the third magnetic blocks 1222 magnetized in the circumferential direction and the plurality of the first magnetic blocks 1221 magnetized in the circumferential direction parallel to the axis of the first magnet 122 are alternately disposed along the circumference of the first magnet 122. The magnetization directions of the adjacent first magnetic blocks 1221 are opposite. For example, the magnetization directions of one of the adjacent first magnets 122 are oriented from the side of the first magnetic blocks 1221 away from the disc-shaped portion 1241 toward the side of the disc-shaped portion 1241, and the magnetization direction of the other one is oriented from the side of the first magnetic blocks 1221 away from the disc-shaped portion 1241 toward the side of the disc-shaped portion 1241. The magnetization directions of the adjacent third magnetic blocks 1222 are opposite in the circumference of the first magnet 122.

Correspondingly, the second magnet 123 further includes a plurality of fourth magnetic blocks 1232 magnetized along the circumferential direction of the second magnet 123, and the plurality of the fourth magnetic blocks 1232 and the plurality of the second magnetic blocks 1231 are alternately arranged along the circumference of the second magnet 123. The magnetization directions of the adjacent second magnetic blocks 1231 are opposite, and the magnetization directions of the adjacent fourth magnetic blocks 1232 are opposite in the circumference of the second magnet 123.

It should be noted that the magnetization directions of the third magnetic blocks 1222 and the fourth magnetic blocks 1232 are not limited to circumferential magnetization. In some embodiments, the magnetization directions of the third magnetic blocks 1222 and the fourth magnetic blocks 1232 may be inclined with respect to the axis of the rotating shaft 121.

In one embodiment, the first magnet 122 and the second magnet 123 are each provided with eight magnetic blocks, that is, the number of the first magnetic blocks 1221, the second magnetic blocks 1231, the third magnetic block 1222, and the fourth magnetic block 1232 are all four. The first magnetic blocks 1221, the second magnetic blocks 1231, the third magnetic blocks 1222, and the fourth magnetic blocks 1232 are all fan-ring magnets. The first magnet 122 and the second magnet 123 are substantially ring-shaped. It will be understood that in other embodiments, the first magnet 122 and the second magnet 123 may also be composed of more or less magnetic blocks, such as two, four, six, or ten, etc.

In order to facilitate the mounting of the first magnet 122 and the second magnet 123, the flywheel 124 is further provided with an identification portion 1243 configured to determine the mounting position of the first magnetic blocks 1221 and the mounting position of the second magnetic blocks 1231. The identification portion 1243 may be configured as a groove, a scale line, an identification, or the like. When the first magnetic blocks 1221 and the second magnetic blocks 1231 are mounted, as long as the positions of one of the first magnetic blocks 1221 and the second magnetic blocks 1231 are identified by the identification portion 1243, the mounting position of the remaining magnetic blocks can be determined, thereby facilitating the mounting of the first magnet 122 and the second magnet 123. Specifically, the identification portion 1243 may be provided on at least one of the tubular portion 1242 and the disc-shaped portion 1241. Specifically, in the illustrated embodiment, both end faces of both ends of the tubular portion 1242 are provided on the identification portion 1243.

Figure 10:
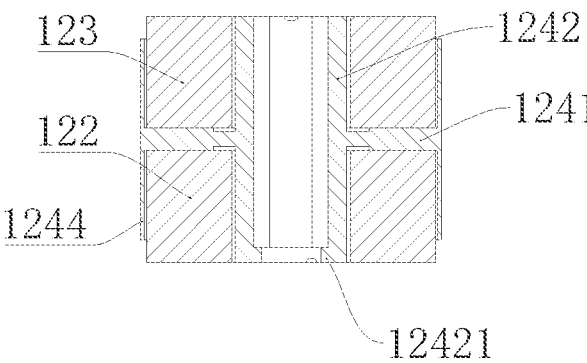
FIG. 10 is a cross-sectional view of the flywheel, the first magnet and the second magnet shown in FIG. 9 taken along the line C-C.
Figure 11:
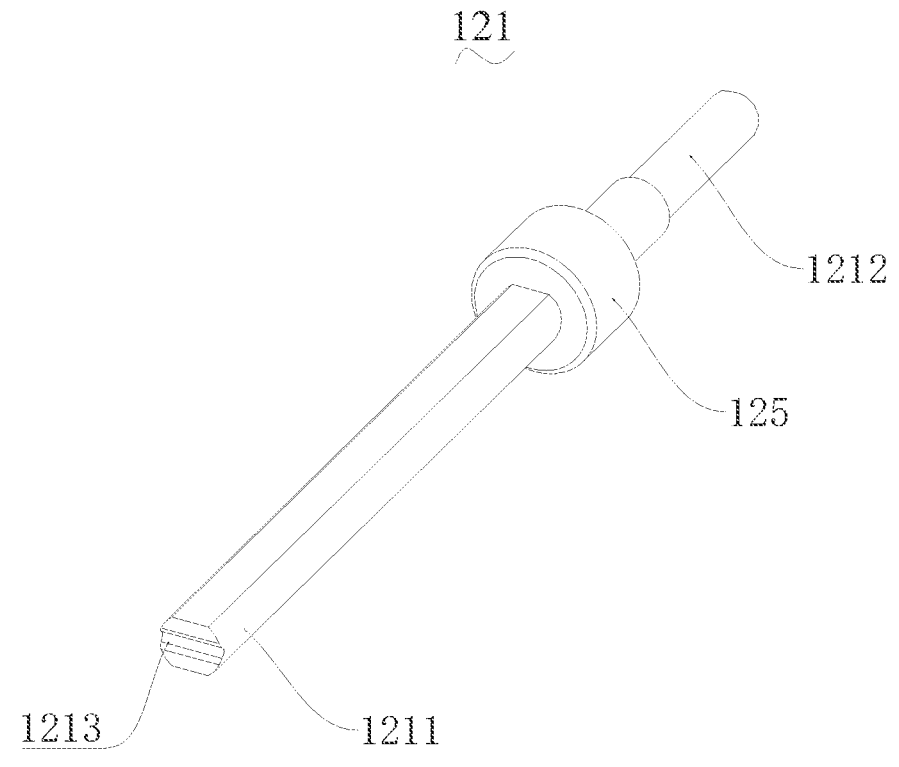
FIG. 11 is a schematic structural view of the rotating shaft shown in FIG. 3.

In one embodiment, the flywheel 124 is fixed to the rotating shaft 121 by adhesive. Referring to FIG. 10 and FIG. 11, an end of the first end 1211 of the rotating shaft 121 is provided with a dispensing groove 1213, and an inner wall of the tubular portion 1242 is provided with a stop protrusion 12421 abutting against the dispensing groove 1213. As such, the glue can be arranged in the dispensing groove 1213 to facilitate the fixing of the rotating shaft 121 to the stop protrusion 12421.

Further, the dispensing groove 1213 extends in a direction perpendicular to the axial direction of the rotating shaft 121, and an end portion of the dispensing groove 1213 extends to an outer circumferential surface of the rotating shaft 121. This arrangement allows the glue to be arranged in the glue dispensing groove 1213, the glue can overflow to the outer circumferential surface of the rotating shaft 121 to bond the inner circumferential wall of the tubular portion 1242 and the circumferential surface of the rotating shaft 121, such that the rotating shaft 121 and the flywheel 124 can be better fixed. Alternatively, it is also convenient to enable the excess glue bonded between the rotating shaft 121 and the tubular portion 1242 to overflow to the dispensing groove 1213.

Referring to FIG. 6 to FIG. 10, in this embodiment, the flywheel 124 further includes an outer ring wall 1244 surrounding the disc-shaped portion 1241. The outer ring wall 1244, the tubular portion 1242, and the disc-shaped portion 1241 cooperatively enclose a first accommodating portion and a second accommodating portion which can accommodate the first magnet 122 and the second magnet 123, respectively. The first accommodating portion and the second first accommodating portion are separated by the disc-shaped portion 1241. Such arrangement can limit the first magnet 122 and the second magnet 123, which not only facilitates the mounting of the first magnet 122 and the second magnet 123, but also makes the combination of the first magnet 122 and the second magnet 123 to the flywheel 124 more stable.

In one embodiment, in the axial direction of the tubular portion 1242, a side of the first magnet 122 away from the disc-shaped portion 1241 is higher than the outer ring wall 1244 by a distance, and a side of the second magnet 123 away from the disc-shaped portion 1241 is higher than the outer ring wall 1244 by a distance, so as to facilitate the assembling of the first magnet 122 and the second magnet 123 on the flywheel 124.

It should be noted that the flywheel 124 is not limited to the above structure. In some embodiments, the flywheel 124 does not have the outer ring wall 1244. In some embodiments, the flywheel 124 does not have the outer ring wall 1244 and a tubular portion 1242, at this time the rotating shaft 121 fixedly extends through the disc-shaped portion 1241, e.g., the center of the disc-shaped portion 1241. Compared with the flywheel 124 having only the disc-shaped portion 1241, the flywheel 124 with the tubular portion 1242 is more stably connected to the rotating shaft 121.

The structure of the power stator 132 is similar to the structure of the driving stator 131. The power stator 132 includes a second back plate 1321, a plurality of second magnetic cores 1322, and a plurality of second coils 1323. The plurality of the second magnetic cores 1322 are spaced one cycle around the rotating shaft 121, and an extending direction of each of second magnetic cores 1322 is parallel to the axis of the rotating shaft 121. One end of each of the second magnetic cores 1322 is fixedly connected to the second back plate 1321, and the other end extends adjacent to the second magnet 123. In other words, in the axial direction of the rotating shaft 121, the driving stator 131 and the power stator 132 are oppositely arranged. Each of the second coils 1323 is wound around corresponding the second magnetic cores 1322. The second coils 1323 is capable of generating a rotating magnetic field that interacts with the second magnet 123.

The first magnetic cores 1312 and the second magnetic cores 1322 include magnetic columns. The first coils 1313 are wound on the magnetic column of the first magnetic cores 1312, and the second coils 1323 is wound on the magnetic column of the second magnetic cores 1322. A cross-sectional area of the magnetic column of the first magnetic cores 1312 is greater than a cross-sectional area of the magnetic column of the second magnetic cores 1322.

The greater the cross-sectional area of the magnetic column is, the larger the generated magnetic flux is, the larger the torque of the stator to the magnet is, and the smaller the required current is, which is beneficial to reduce power consumption and heat generation. Since the rotating shaft 121 extends through the middle portion of the power stator 132, the cross-sectional area of the second magnetic cores 1322 is limited due to the radial dimension of the blood pump 100. Since no rotating shaft 121 extends through the middle portion of the driving stator 131, the first magnetic cores 1312 can select a greater cross-sectional area. In other words, this arrangement can reduce the power consumption and reduce the heat generated by the driving device 10.

In one embodiment, both the first magnetic cores 1312 and the second magnetic cores 1322 have only a magnetic column, that is, neither the first magnetic cores 1312 nor the second magnetic cores 1322 has a head (that is, a pole piece) with a large width. In a length direction of the first magnetic cores 1312 and the second magnetic cores 1322, the width of the first magnetic cores 1312 and the second magnetic cores 1322 is constant. The entire first magnetic cores 1312 can be magnetically coupled to the first magnet 122, and the entire second magnetic cores 1322 can be magnetically coupled to the second magnet 123. Compared with the magnetic core provided with the pole shoe, the entire magnetic core of the present application can reduce the magnetic loss, increase the magnetic coupling density between the first magnetic cores 1312 and the first magnet 122, the second magnetic cores 1322 and the second magnet 123, so as to increase the torque of the driving stator 131 to the first magnet 122 (under the condition of equal current) and the torque of the power stator 132 to the second magnet 123 (under the condition of equal current). In addition, the first magnetic cores 1312 and the second magnetic cores 1322 without the head can also greatly reduce the problem of motor power reduction caused by a local magnetic short circuit caused by contact between adjacent magnetic cores.

Figure 12:
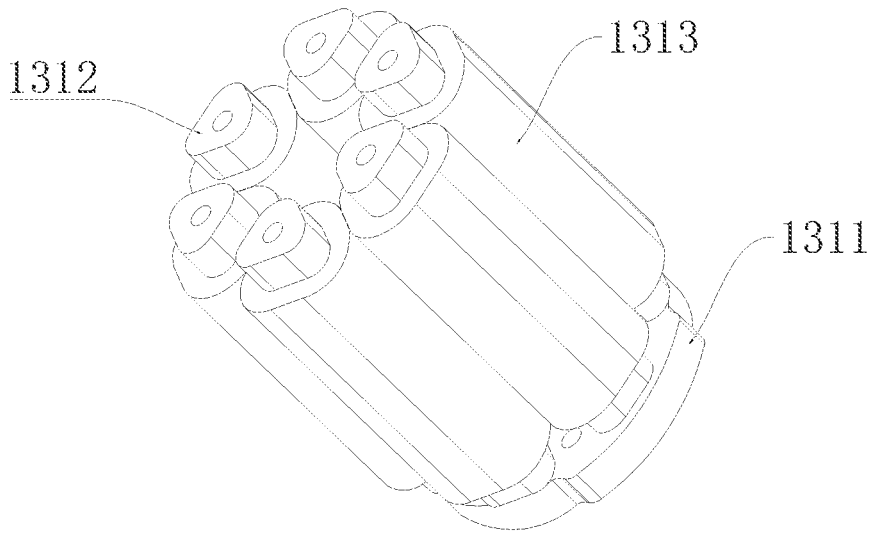
FIG. 12 is a schematic structural view of the driving stator of the driving device shown in FIG. 4.

The shape of the cross-section of the first magnetic cores 1312 and the second magnetic cores 1322 having only the magnetic column may be a sector, a circle, a trapezoid, a sector ring, or the like. As it is shown in FIG. 12, in the illustrated embodiment, the first magnetic cores 1312 and the second magnetic cores 1322 having only magnetic columns are substantially triangular prism-shaped, and one edge of each magnetic core faces the axis of the rotating shaft 121. In one embodiment, the edges of the first magnetic cores 1312 and the second magnetic cores 1322 are subjected to chamfer treatment, and the subsequent winding of the coil can be facilitated by chamfer treatment of the edges, and the insulating material coated on the coil can be protected.

It can be understood that, in other embodiments, the first magnetic cores 1312 and the second magnetic cores 1322 may further include a head portion disposed at one end of the magnetic column. The first back plate 1311 is engaged with one end of the magnetic column of the first magnetic cores 1312 away from the head portion, and the second back plate 1321 is engaged with an end of the magnetic column of the second magnetic cores 1322 away from the head. Alternatively, in some embodiments, one of the first magnetic cores 1312 and the second magnetic cores 1322 may have both the magnetic column and the head, and the other has only the magnetic column.

Figure 13:
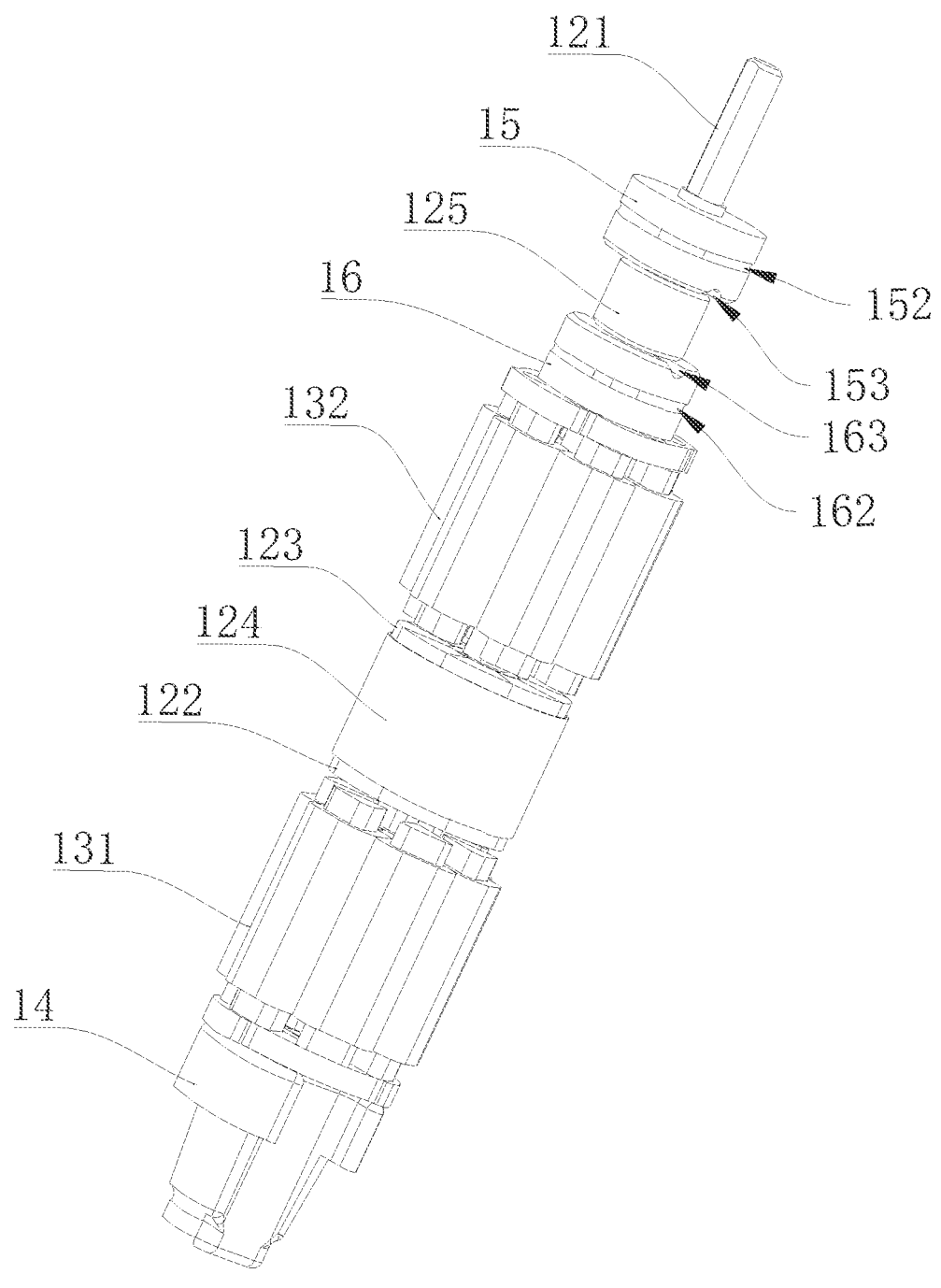
FIG. 13 is a schematic structural view of the driving device shown in FIG. 4 in another aspect after omitting the driving housing.

Referring to FIG. 3, FIG. 5, and FIG. 13, the driving device 10 further includes a first shaft sleeve 15, and the first shaft sleeve 15 is fixedly connected to the driving housing 11. The rotating shaft 121 can rotatably extend through the first shaft sleeve 15. A gap is provided between the rotating shaft 121 and the first shaft sleeve 15. By providing the first shaft sleeve 15, the assembly size requirements of the rotating shaft 121 and the driving housing 11 can be reduced, while reducing the rotational friction of the rotating shaft 121.

In order to facilitate fixing and mounting of the first shaft sleeve 15 in the driving housing 11, a first glue groove 152 is provided on the outer peripheral surface of the first shaft sleeve 15. The provision of the first glue groove 152 can be conveniently arranged in the first glue groove 152, so as to bond the first shaft sleeve 15 and the driving housing 11 together.

In one embodiment, the first shaft sleeve 15 is disposed at the communication port 110, and the gap between the first shaft sleeve 15 and the rotating shaft 121 is less than or equal to 2 µm. Since it is difficult for the smallest red blood cells (about 8 µm in diameter and about 2 µm in thickness) to enter the gap with a width less than or equal to 2 µm, the flow of blood through the communication port 110 is prevented from entering the inside of the driving housing 11 by the backwashing of the perfusion fluid through this gap.

In order to avoid contamination of the perfusion fluid and/or corrosion of the elements in the driving device 10, the driving stator 131 and the power stator 132 of the driving device 10 are covered with a waterproof sealing film. The waterproof sealing film may be the glue solidifies formed after silicone gel, a waterproof film, etc.

The driving device 10 further includes a second shaft sleeve 16, and the second shaft sleeve 16 is fixedly connected to the driving housing 11. The rotating shaft 121 can rotatably extend through the second shaft sleeve 16. The second shaft sleeve 16 and the first shaft sleeve 15 are spaced along the extending direction of the rotating shaft 121, and the first shaft sleeve 15 is located more adjacent to the impeller 30 than the second shaft sleeve 16. By adding the second sleeve 16 on the basis of the first sleeve 15, the rotational stability of the rotating shaft 121 can be improved.

In order to facilitate fixing the second shaft sleeve 16 in the driving housing 11, a second glue groove 162 is provided on the outer peripheral surface of the second shaft sleeve 16. The provision of the second glue groove 162 may facilitate the bonding of the second sleeve 16 and the driving housing 11 together by providing an adhesive in the first glue groove 152.

Specifically, the first shaft sleeve 15 and the second shaft sleeve 16 are metal shaft sleeve, ceramic shaft sleeve, or the like. Further, both of the first shaft sleeve 15 and the second shaft sleeve 16 are ceramic shaft sleeve, which are more corrosion-resistant, have a long service life, and are lighter in weight.

Referring to FIG. 3, FIG. 5 and FIG. 13, in one embodiment, the rotor 12 further includes a limiting ring 125 fixedly sleeved on the rotating shaft 121. The limiting ring 125 may be integrally formed with the rotating shaft 121, or may be fixed to the rotating shaft 121 by bonding, welding, or the like. The limiting ring 125 is located between the first shaft sleeve 15 and the second shaft sleeve 16, and the outer diameter of the limiting ring 125 is greater than the inner diameter of the first shaft sleeve 15. At the same time, the outer diameter of the limiting ring 125 is greater than the inner diameter of the second shaft sleeve 16, so as to limit the rotating shaft 121 in the extending direction of the rotating shaft 121, and prevent the rotating shaft 121 from greatly moving with respect to the driving housing 11 in the extending direction of the rotating shaft 121.

Figure 14:
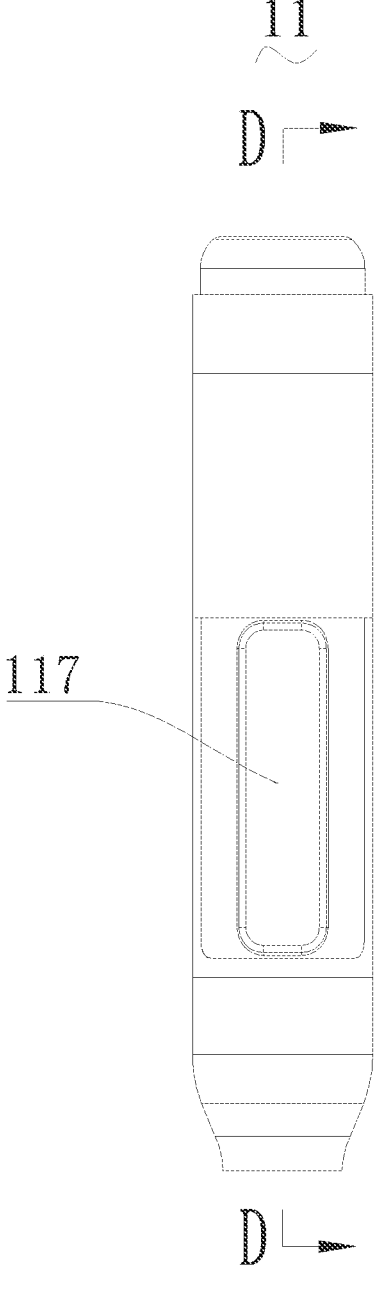
FIG. 14 is a schematic structural view of the driving housing of the blood pump shown in FIG. 1.
Figure 15:
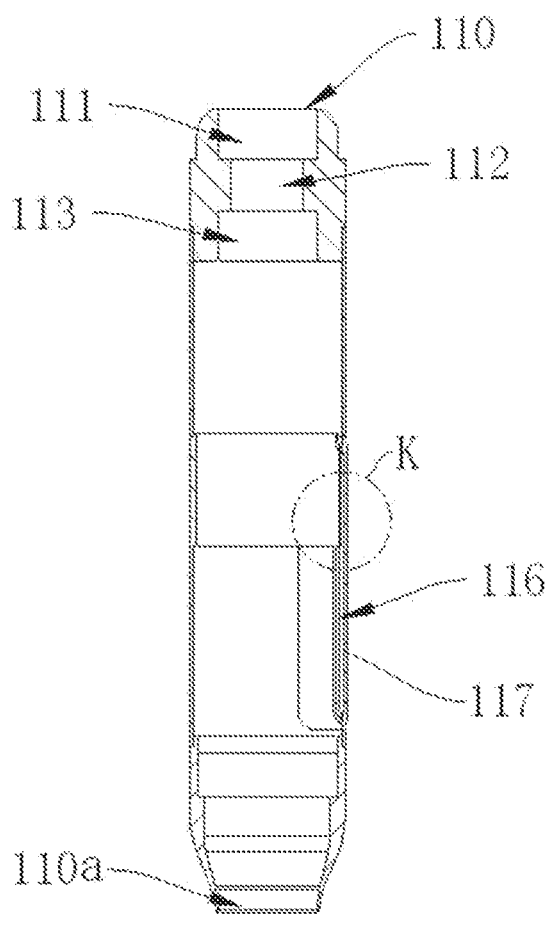
FIG. 15 is a cross-sectional view of the driving housing shown in FIG. 14 taken along the line D-D.
Figure 16:
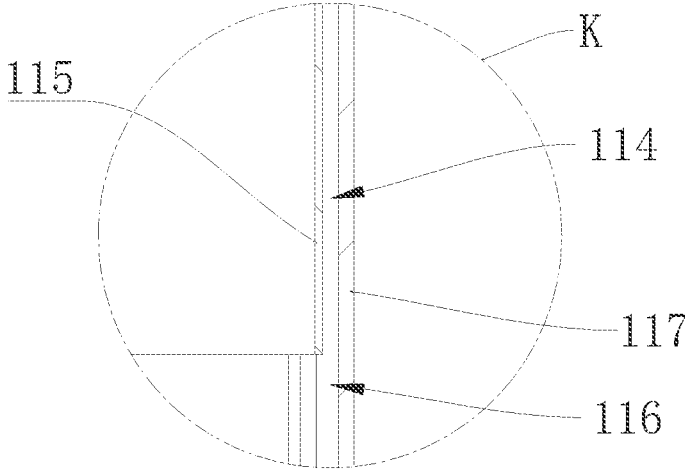
FIG. 16 is a partially enlarged view of a portion K of the driving housing shown in FIG. 15.
Figure 17:
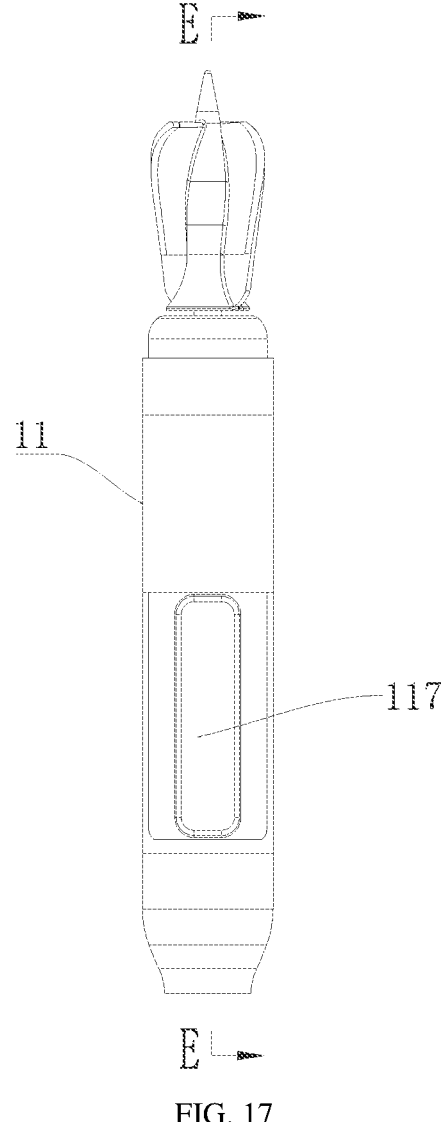
FIG. 17 is a schematic structural view of the blood pump shown in FIG. 1 after omitting the sleeve assembly and the catheter assembly.
Figure 18:
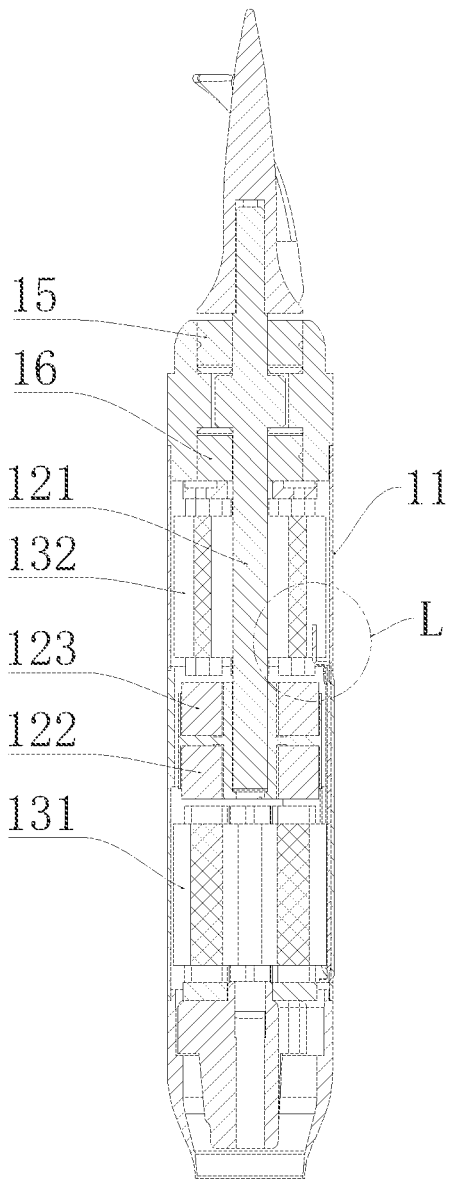
FIG. 18 is a cross-sectional view of the blood pump shown in FIG. 17 taken along the line E-E.
Figure 19:
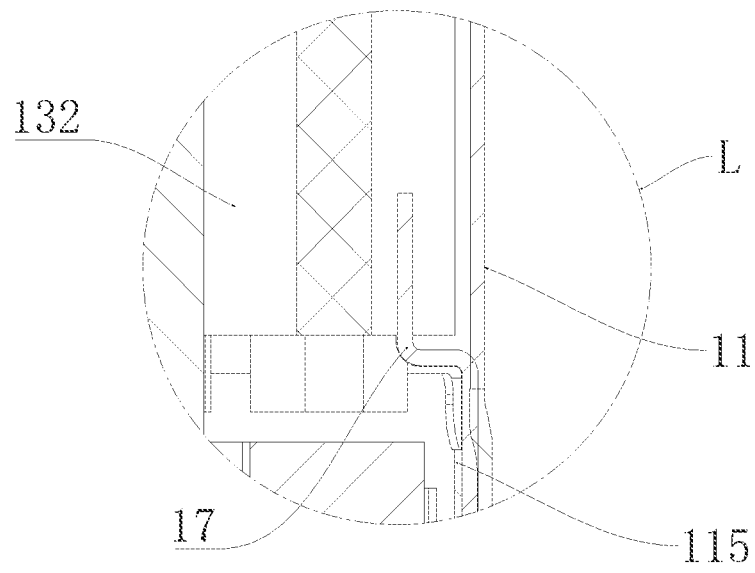
FIG. 19 is a partial enlarged view of the portion L in FIG. 18.

Referring to FIG. 3, FIG. 14, and FIG. 15, specifically, the driving housing 11 is provided with a first limiting hole 111, a second limiting hole 112, and a third limiting hole 113 that are sequentially arranged in along the axis of the rotating shaft 121. The second limiting hole 112 is in communication with the first limiting hole 111. The third limiting hole 113 is in communication with the second limiting hole 112. A diameter of the second limiting hole 112 is less than a diameter of the first limiting hole 111 and is less than a diameter of the third limiting hole 113. The first shaft sleeve 15 is accommodated in the first limiting hole 111, the second shaft sleeve 16 is accommodated in the third limiting hole 113, and the limiting ring 125 is accommodated in the second limiting hole 112. By providing the first limiting hole 111, the second limiting hole 112, and the third limiting hole 113, the first shaft sleeve 15 and second shaft sleeve 16 can be limited in the axial direction of the rotating shaft 121. The communication port 110 is an opening on the side of the first limiting hole 111 away from the second limiting hole 112.

In this embodiment, the limiting ring 125 and the hole wall of the first limiting hole 111 are in clearance fit.

The perfusion liquid flowing from the perfusion pipeline 411 into the interior of the driving housing 11 flows through the gap between the second shaft sleeve 16 and the rotating shaft 121, the gap between the limiting ring 125 and the first limiting hole 111, and the gap between the first shaft sleeve 15 and the rotating shaft 121, and enters the interior of the sleeve assembly 20 from the communication port 110, which not only functions as a backwash, but also functions as a lubrication between the rotating shaft 121 and the first shaft sleeve 15, and between the rotating shaft 121 and the second shaft sleeve 16.

Referring to FIG. 13 again, in this embodiment, a side of the first shaft sleeve 15 adjacent to the limiting ring 125 is provided with a first fluid groove 153, and the first fluid groove 153 is in communication with the gap between the first shaft sleeve 15 and the rotating shaft 121. A side of the second sleeve 16 adjacent to the limiting ring 125 is provided with a second fluid groove 163, and the second fluid groove 163 is in communication with the gap between the second shaft sleeve 16 and the rotating shaft 121. As such, it facilitates circulation of cleaning fluid. It should be noted that, in other embodiments, one of the first shaft sleeve 15 and the second shaft sleeve 16 may be provided with a fluid groove, the other one is not provided with a fluid groove.

Referring to FIG. 14 to FIG. 19, further, a protection member 115 is fixedly arranged in the driving housing 11. An accommodation gap 114 is formed and between the protection member 115 and the side wall of the driving housing 11, which is capable of accommodating an electric wire 17 connected to the power stator 132. The electric wire 17 may be directly connected to the electrical connection line of the supply line, alternatively, the electric wire 17 may be directly electrically connected to the external control of the blood pump 100. The position of the protection member 115 corresponds to the position of the first magnet 122 and the second magnet 123, so as to separate the first magnet 122 and the second magnet 123 from the accommodation gap 114. By providing the accommodation gap 114, it can be avoided that during the rotation of the rotor 12, the electric wire 17 comes into contact with the first magnet 122 and the second magnet 123, which causes the electric wire 17 to be twisted off with the rotation of the magnet. In this embodiment, both of the first magnet 122 and the second magnet 123 are mounted in the flywheel 124, and the protection member 115 is disposed between the flywheel 124 and the side wall of the driving housing 11. The protection member 115 separates the flywheel 124 from the electric wire 17, so as to prevent the electric wire 17 from breaking or falling off due to the contact of the electric wire 17 with the flywheel 124.

Figure 20:
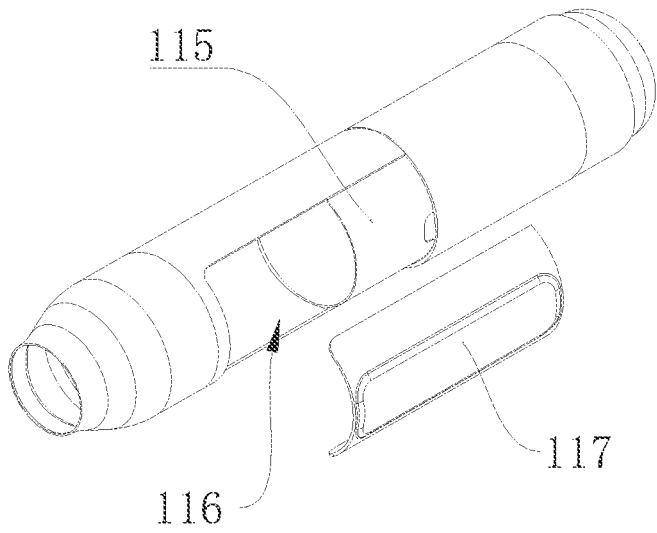
FIG. 20 is an exploded view of the driving housing shown in FIG. 14.

Referring to FIG. 20, in order to facilitate the mounting of the electric wire 17 connecting the driving stator 131 and the power stator 132, the driving housing 11 is further provided with a mounting opening 116. The driving housing 11 further includes a cover 117 configured to seal the mounting opening 116. The protection member 115 shields a part of the mounting opening 116, and the accommodation gap 114 is formed between the cover 117 and the protection member 115.

It should be noted that, in order to prevent the electric wire 17 from rotating with the magnet, the manner of providing the protection member 115 is not limited. In some embodiments, a passage for the electric wire 17 to extend through may also be directly provided on the side wall of the driving housing 11. In this case, the protection member 115 does not need to be provided.

Figure 21:
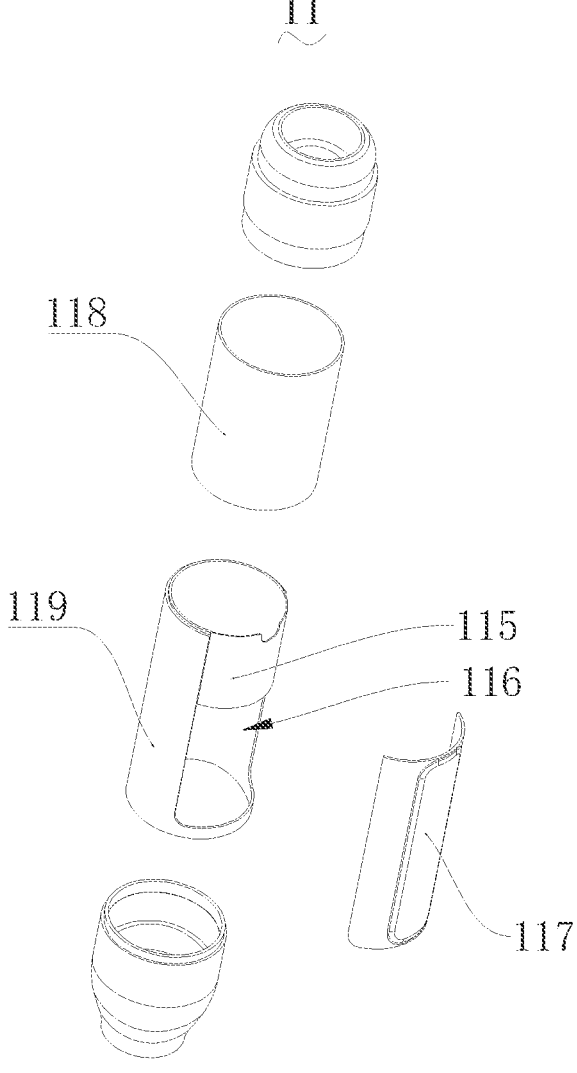
FIG. 21 is another exploded view of the driving housing shown in FIG. 20.

Referring to FIG. 21, the driving housing 11 includes a first housing 118 and a second housing 119 connected to the first housing 118, and the protection member 115 and the mounting opening 116 are both located on the second housing 119. By designing the driving housing 11 into a multi-housing combination, it can facilitate assembly of the internal parts of the driving device 10.

It should be noted that the driving device 10 is not limited to the above structure. In some embodiments, the driving device 10 has two flywheels, and the power stator 132 is located between the two flywheels, that is, one flywheel is located between the impeller 30 and the power stator 132, the other flywheel is located between the power stator 132 and the driving stator 131. The first magnet 122 is fixed on the flywheel between the power stator 132 and the driving stator 131, and the second magnet 123 is fixed on the flywheel between the impeller 30 and the power stator 132. At this time, if the protection member 115 is provided, the protection member 115 is provided between the flywheel between the power stator 132 and the driving stator 131 and the driving housing 11, that is, the position of the protection member 115 corresponds to the position of the first magnet 122. At this time, the protection member 115 is located between the flywheel on which the first magnet 122 is mounted and the electric wire 17. It should be understood that, the rotor 12 may not have a flywheel, at this time, the protection member 115 is located between the first magnet 122 and the electric wire 17.

Alternatively, in some embodiments, the two flywheels are both located between the power stator 132 and the driving stator 131, and the two flywheels are respectively configured to mount the first magnet 122 and the second magnet 123. In this case, if the protection member 115 is provided, the protection member 115 is disposed between the flywheel on which the first magnet 122 is mounted and the electric wire 17, and between the flywheel on which the second magnet 123 is mounted and the electric wire 17. It should be understood that, the rotor 12 may not have the flywheel. In this case, the protection member 115 is provided between the first magnet 122 and the electric wire 17, and between the second magnet 123 and the electric wire 17.

In some embodiments, the blood pump 100 has only the driving stator 131, and has no power stator 132, in that case, the protection member 115 may not be provided.

While the disclosed subject matter has been described with reference to illustrative embodiments, this description is not intended to be construed in a limiting sense. Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A driving device, comprising:
a driving housing;
a rotor comprising a rotating shaft and a first magnet, an end of the rotating shaft being accommodated in the driving housing, the first magnet being fixedly connected to the rotating shaft; and
a stator mechanism accommodated in the driving housing, the stator mechanism comprising a driving stator, the driving stator and the rotating shaft being spaced along an axis of the rotating shaft, the driving stator being capable of generating a rotating magnetic field interacting with the first magnet, such that the first magnet is capable of driving the rotating shaft to rotate about the axis of the rotating shaft,
wherein the stator mechanism further comprises a power stator, the power stator and the driving stator are provided along the axis of the rotating shaft, the rotating shaft is capable of rotatably extending through the power stator, the rotor further comprises a second magnet fixedly connected to the rotating shaft, and the power stator is capable of generating a rotating magnetic field interacting with the second magnet.

2. The driving device according to claim 1, wherein the rotor further comprises a flywheel fixedly connected to the rotating shaft, the flywheel is located between the power stator and the driving stator, and both of the first magnet and the second magnet are arranged on the flywheel.

3. The driving device according to claim 2, wherein the flywheel comprises a disc-shaped portion and a tubular portion, the tubular portion fixedly extends through a middle portion of the disc-shaped portion and is coaxially with the disc-shaped portion, and an end of the rotating shaft away from the impeller is fixedly accommodated in the tubular portion, and the first magnet and the second magnet are arranged on opposite sides of the disc-shaped portion, respectively.

4. The driving device according to claim 3, wherein the flywheel further comprises an outer ring wall surrounding the disc-shaped portion, the outer ring wall, the tubular portion, and the disc-shaped portion cooperatively enclose a first accommodating portion and a second accommodating portion to accommodate the first magnet and the second magnet, respectively, and the first accommodating portion and the second accommodating portion are separated by the disc-shaped portion.

5. The driving device according to claim 2, wherein the flywheel comprises a disc-shaped portion, and the rotating shaft fixedly extends through the disc-shaped portion, the first magnet and the second magnet are arranged on opposite sides of the disc-shaped portion, respectively, both of the first magnet and the second magnet are ring-shaped Halbach array magnets, the first magnet comprises a plurality of first magnetic blocks whose magnetic charging directions are parallel to an axis of the first magnet, the second magnet comprises a plurality of second magnetic blocks whose magnetic charging directions are parallel to an axis of the second magnet, the plurality of the second magnetic blocks and the plurality of the first magnetic blocks are respectively arranged on opposite sides of the disc-shaped portion surrounding the rotating shaft, in an extending direction of the rotating shaft, each of the second magnetic blocks is arranged opposite to one of the first magnetic blocks, and sides of the oppositely arranged first magnetic blocks and second magnetic blocks facing the disc-shaped portion have opposite polarities.

6. The driving device according to claim 5, wherein the flywheel is further provided with an identification portion configured to determine a mounting position of the first magnetic blocks and a mounting position of the second magnetic blocks.

7. The driving device according to claim 1, wherein the driving stator comprises a plurality of first magnetic cores and a plurality of first coils respectively wound around the first magnetic cores, the plurality of the first magnetic cores are spaced one cycle around the axis of the rotating shaft, the power stator comprises a plurality of second magnetic cores and a plurality of second coils respectively wound around the plurality of the second magnetic cores, and the plurality of the second magnetic cores are spaced one cycle around the rotating shaft.

8. The driving device according to claim 7, wherein each of the first magnetic core and the second magnetic core comprises a magnetic column, the first coil is wound around the magnetic column of the first magnetic core, the second coil is wound around the magnetic column of the second magnetic core, and a cross-sectional area of the magnetic column of the first magnetic core is greater than a cross-sectional area of the magnetic column of the second magnetic core.

9. The driving device according to claim 1, wherein the first magnet is arranged between the driving stator and the power stator, a protection member is fixedly arranged in the driving housing, and an accommodation gap capable of accommodating an electrical wire connected to the power stator is formed between the protection member and a side wall of the driving housing, a position of the protection member corresponds to a position of the first magnet, and the protection member is located between the first magnet and the electrical wire.

10. The driving device according to claim 9, wherein the driving housing is further provided with a mounting opening, the driving housing further comprises a cover configured to seal the mounting opening, the protection member shields a part of the mounting opening, and the accommodation gap is formed between the cover and the protection member.

11. The driving device according to claim 1, wherein the driving device further comprises a first shaft sleeve and a second shaft sleeve, both of the first shaft sleeve and the second shaft sleeve are fixedly connected to the driving housing, the rotating shaft rotatably extends through the first shaft sleeve and the second shaft sleeve, the rotor further comprises a limiting ring fixedly sleeved on the rotating shaft, the limiting ring is located between the first shaft sleeve and the second shaft sleeve, an outer diameter of the limiting ring is respectively greater than an inner diameter of the first shaft sleeve and an inner diameter of the second shaft sleeve, so as to limit the rotating shaft in an extending direction of the rotating shaft.

12. The driving device according to claim 11, wherein the first shaft sleeve is a metal shaft sleeve or a ceramic shaft sleeve; and/or the second shaft sleeve is a metal shaft sleeve or a ceramic shaft sleeve.

13. The driving device according to claim 11, wherein a side of the first shaft sleeve adjacent to the limiting ring is provided with a first fluid groove, the first fluid groove is in communication with a gap between the first shaft sleeve and the rotating shaft; and/or a side of the second shaft sleeve adjacent to the limiting ring is provided with a second fluid groove, and the second fluid groove is in communication with a gap between the second shaft sleeve and the rotating shaft.

14. The driving device according to claim 1, wherein the driving housing has a communication port, the driving device further comprises a shaft sleeve fixedly connected to the driving housing, and the shaft sleeve is arranged at the communication port, the rotating shaft rotatably extends through the shaft sleeve, wherein a gap between the shaft sleeve and the rotating shaft is less than or equal to 2 μm.

15. The driving device according to claim 1, wherein the driving housing has a communication port and a docking port, the communication port is capable of being in communication with a sleeve assembly configured to accommodate an impeller, and the docking port is capable of being in communication with a perfusion pipeline, such that perfusion liquid is capable of flowing through the driving housing through the perfusion pipeline, and flowing into the sleeve assembly from the communication port.

16. The driving device according to claim 1, wherein the driving stator comprises a first back plate, a plurality of first magnetic cores, and a plurality of first coils respectively wound around the first magnetic cores, the first back plate is fixedly connected to the driving housing, the plurality of the first magnetic cores are spaced one cycle around the axis of the rotating shaft, one ends of the plurality of the first magnetic cores are fixedly connected to the first back plate, and the other ends of the first magnetic cores extends in a direction adjacent to the first magnet.

17. The driving device according to claim 16, wherein the first back plate is provided with a positioning hole, the driving device further comprises a fixing member fixed in the driving housing, the fixing member is provided with a positioning column, and the positioning column extends through the positioning hole.

18. A blood pump, comprising:

the driving device according to claim 1; and an impeller fixedly connected to the rotating shaft and capable of rotating with the rotating shaft.

* * * * *